US011707179B2

(12) United States Patent
Gliner et al.

(10) Patent No.: US 11,707,179 B2
(45) Date of Patent: *Jul. 25, 2023

(54) AUTOMATIC PROBE REINSERTION

(71) Applicant: Biosense Webster (Israel) Ltd., Yokneam (IL)

(72) Inventors: Vadim Gliner, Haifa (IL); Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/568,766

(22) Filed: Jan. 5, 2022

(65) Prior Publication Data

US 2022/0202509 A1 Jun. 30, 2022

Related U.S. Application Data

(63) Continuation of application No. 16/152,209, filed on Oct. 4, 2018, now Pat. No. 11,229,492.

(51) Int. Cl.
*A61B 1/00* (2006.01)
*A61B 34/30* (2016.01)
(Continued)

(52) U.S. Cl.
CPC ...... *A61B 1/00006* (2013.01); *A61B 1/00055* (2013.01); *A61B 1/000096* (2022.02);
(Continued)

(58) Field of Classification Search
CPC ............ A61B 1/00006; A61B 1/00009; A61B 1/00055; A61B 1/00149; A61B 1/121;
(Continued)

(56) References Cited

U.S. PATENT DOCUMENTS 5,829,444 A 11/1998 Ferre et al.
7,720,521 B2 5/2010 Chang et al.
(Continued)

FOREIGN PATENT DOCUMENTS

JP 2009-056239 A 9/2007
JP 2008-220709 A 9/2008
(Continued)

OTHER PUBLICATIONS

Pertuz, Said, Domenec Puig, and Miguel Angel Garcia. "Analysis of focus measure operators for shape-from-focus." *Pattern Recognition* 46.5 (2013): 1415-1432.
(Continued)

*Primary Examiner* — Anh Tuan T Nguyen
*Assistant Examiner* — Sung Ham
(74) *Attorney, Agent, or Firm* — Frost Brown Todd LLP

(57) ABSTRACT

In accordance with one embodiment, an automated probe system includes a probe configured to be reversibly inserted into a live body part, a robotic arm attached to the probe and configured to manipulate the probe, a first sensor configured to track movement of the probe during an insertion and a reinsertion of the probe in the live body part, a second sensor configured to track movement of the live body part, and a controller configured to calculate an insertion path of the probe in the live body part based on the tracked movement of the probe during the insertion, and calculate a reinsertion path of the probe based on the calculated insertion path while compensating for the tracked movement of the live body part, and send control commands to the robotic arm to reinsert the probe in the live body part according to the calculated reinsertion path.

20 Claims, 6 Drawing Sheets

(51) Int. Cl.
*A61B 1/12* (2006.01)
*A61B 5/06* (2006.01)
*A61B 34/10* (2016.01)
*A61B 34/20* (2016.01)

(52) U.S. Cl.
CPC .......... *A61B 1/00149* (2013.01); *A61B 1/121* (2013.01); *A61B 5/062* (2013.01); *A61B 5/065* (2013.01); *A61B 34/30* (2016.02); *A61B 2034/107* (2016.02); *A61B 2034/2051* (2016.02); *A61B 2034/301* (2016.02)

(58) Field of Classification Search
CPC .......... A61B 1/233; A61B 5/06; A61B 5/061; A61B 5/062; A61B 5/065; A61B 34/30; A61B 34/70; A61B 34/76; A61B 2034/107; A61B 2034/2051; A61B 2034/301; A61B 6/032; A61B 6/12; A61B 6/486; A61B 1/00057; A61B 1/00091; A61B 1/00096; A61B 1/0016; A61B 5/6868; A61B 5/6819; A61B 90/50; A61B 1/126; G05B 19/423
See application file for complete search history.

(56) References Cited

U.S. PATENT DOCUMENTS

| | | | |
|---|---|---|---|
| 8,306,656 | B1 | 11/2012 | Schaible et al. |
| 11,229,492 | B2 | 1/2022 | Gliner et al. |
| 2001/0025142 | A1 | 9/2001 | Wessels et al. |
| 2007/0265526 | A1 | 11/2007 | Govari et al. |
| 2011/0137153 | A1 | 6/2011 | Govari et al. |
| 2013/0331730 | A1* | 12/2013 | Fenech ............... A61M 13/003 600/560 |
| 2014/0171792 | A1 | 6/2014 | Dalal et al. |
| 2015/0073265 | A1 | 3/2015 | Popovic et al. |
| 2015/0223670 | A1 | 8/2015 | Fujita et al. |
| 2016/0302653 | A1 | 10/2016 | Inoue |
| 2017/0303770 | A1* | 10/2017 | Takahashi .......... A61B 1/00048 |
| 2017/0333155 | A1 | 11/2017 | Azizian et al. |
| 2018/0049808 | A1 | 2/2018 | Krimsky |
| 2018/0344418 | A1 | 12/2018 | Komuro |
| 2019/0053861 | A1* | 2/2019 | Lwin .................... A61B 1/0052 |
| 2019/0328620 | A1 | 10/2019 | Cohen et al. |
| 2020/0046434 | A1* | 2/2020 | Graetzel ................ A61B 34/30 |

FOREIGN PATENT DOCUMENTS

| | | |
|---|---|---|
| JP | 2012-024518 A | 10/2017 |
| WO | WO 2001/097694 A1 | 12/2001 |

OTHER PUBLICATIONS

European Search Report and Written Opinion dated Jan. 17, 2020, for Application No. 19201257.3, 9 pages.

European Communication dated Aug. 18, 2022, for Application No. 19201257.3, 6 pages.

\* cited by examiner

AUTOMATIC PROBE REINSERTION

This application is a continuation of U.S. patent application Ser. No. 16/152,209, filed Oct. 4, 2018, and issued as U.S. Pat. No. 11,229,492 on Jan. 25, 2022.

FIELD OF THE INVENTION

The present invention relates to invasive medical apparatus and methods, and in particular, but not exclusively to, robotic insertion of a probe into a moving body-part.

BACKGROUND

By way of introduction, an endoscope may be used in brain surgery or sinus dilation among other applications. In sinus dilation, an endoscope may be inserted via the nasal cavity through various sinus cavities. In brain surgery, instead of opening skull to remove a tumor, an endoscope may be inserted via the nasal cavity and the sinus cavities.

During use of an endoscope with a robot, for instance in an ear, nose, and throat (ENT) procedure or brain surgery, the front of the endoscope lens typically becomes coated with steam, blood, and dirt, reducing the clarity of the image captured by the endoscope. While there are endoscopes having cleansing jets, physicians often prefer not to use these, since the fluid from the jets bothers the patient. Rather, physicians remove the endoscope, wipe the front of the lens with gauze, then reinsert the endoscope.

Japanese Patent Application Serial Number 2012024518A of Fujifilm Corp. describes a system in which a center line L of a tubular tissue of a subject is acquired from a previously acquired three-dimensional image of the subject and an endoscopic image captured while moving an endoscope inserted in the tubular tissue along the longitudinal direction of the tubular tissue is displayed. When one feature region of the tubular tissue is displayed in the displayed endoscopic image, the reference position of the endoscope is input and a position Q1 corresponding to the one feature region is set on the center line L. The amount of movement and the direction of travel of the endoscope moved further from the reference position are acquired. The position distant by the acquired amount of movement in the acquired direction of travel along the center line from the position Q1 corresponding to the one feature region is calculated as a present position Q2, and an indicator M indicating the calculated present position Q2 is displayed on the center line L.

US Published Patent Application Serial Number 2017/0303770, issued as U.S. Pat. No. 10,750,930 on Aug. 25, 2020, describes an endoscope apparatus configured to be capable of assisting with setting of an angle of view of immediately before an endoscope is pulled out and cleaned and then reinserted during surgery in endoscopic surgery and the like, and a method and program for operating the endoscope apparatus. An image captured by the endoscope apparatus is recorded, a feature value of the image captured is detected, a difference between detected feature values of consecutive images is obtained, and, when the difference is greater than a predetermined threshold value, an index is added to the image captured.

Japanese Patent Application Serial Number 2009056239A of Olympus Medical Systems Corp. describes an endoscope apparatus comprising an endoscope for capturing the image of a celomic tract of a subject, a route setting means for setting the insertion route for inserting the distal end of the endoscope to a concerned region inside the subject from outside of the body cavity based on the three-dimensional image data of the subject, a virtual endoscopic image creating means for creating the virtual endoscopic image of the celomic tract based on the three-dimensional image data of the subject, a position detecting means for detecting the position of the distal end of the endoscope, a re-insertion reroute setting means for setting the re-insertion route partly overlapping the insertion route for inserting the distal end of the endoscope from the distal end position to the concerned region, and an image processing means for composing the image captured by the endoscope, the virtual endoscopic image of the insertion route and the virtual endoscopic image of the re-insertion route.

Some prior attempts describe systems and methods for guided endoscope navigation including a registration module configured to register a first set of images with a second set of images of an endoscope. A selection module is configured to receive selected areas of interest on the first set of images and transform the selected areas of interest to an endoscope coordinate frame. A guidance module is configured to overlay guidance tools onto the second set of images to permit a user of the endoscope to navigate to the selected areas of interest.

SUMMARY

There is provided in accordance with an embodiment of the present disclosure, an automated probe system including a probe configured to be reversibly inserted into a live body part, a robotic arm attached to the probe and configured to manipulate the probe, a first sensor configured to track movement of the probe during an insertion and a reinsertion of the probe in the live body part, a second sensor disposed on the live body-part and configured to track movement of the live body part including movement of the live body-part during the insertion and the reinsertion of the probe in the live body part, and a controller configured to calculate an insertion path of the probe in the live body part based on the tracked movement of the probe during the insertion, and calculate a reinsertion path of the probe based on the calculated insertion path while compensating for the tracked movement of the live body part, and after insertion of the probe along the insertion path, followed by withdrawal of the probe from the live body-part, send a plurality of control commands to the robotic arm to reinsert the probe in the live body part the calculated reinsertion path.

Further in accordance with an embodiment of the present disclosure, the controller is configured to calculate the reinsertion path of the probe based on the calculated insertion path while compensating for the tracked movement of the live body-part during the insertion and the reinsertion of the probe in the live body part.

Still further in accordance with an embodiment of the present disclosure, the controller is configured to calculate a movement-compensated insertion path of the probe in the live body part based on the tracked movement of the probe during the insertion of the probe compensated by the tracked movement of the live body part during the insertion of the probe, and calculate the reinsertion path based on the movement-compensated insertion path further compensated by the tracked movement of the live body part during the reinsertion of the probe in the live body part.

Additionally, in accordance with an embodiment of the present disclosure, the probe includes an endoscope having a lens.

Moreover, in accordance with an embodiment of the present disclosure, the controller is configured to process an image captured by the endoscope so as to detect a blur in the image that is indicative of a need to clean the lens.

Further in accordance with an embodiment of the present disclosure, the controller is configured to send a command to the robotic arm to remove the endoscope from the live body part for cleaning in response to detecting the blur in the image captured by the endoscope.

Still further in accordance with an embodiment of the present disclosure, the system includes a lens cleaning device configured to automatically clean the lens of the endoscope after the endoscope had been removed from the live body-part.

Additionally, in accordance with an embodiment of the present disclosure, the controller is configured to send the plurality of control commands to the robotic arm to reinsert the probe in the live body part the calculated reinsertion path in response to the lens being automatically cleaned.

Moreover, in accordance with an embodiment of the present disclosure, the controller is configured to output a notification that the lens of the endoscope needs cleaning.

Further in accordance with an embodiment of the present disclosure, at least part of the probe is flexible, and wherein the first sensor is disposed on a distal end of the probe.

There is also provided in accordance with another embodiment of the present disclosure, an automated probe method including tracking movement of a probe during an insertion and a reinsertion of the probe in a live body part, tracking movement of the live body part including movement of the live body-part during the insertion and the reinsertion of the probe in the live body part, calculating an insertion path of the probe in the live body part based on the tracked movement of the probe during the insertion, calculating a reinsertion path of the probe based on the calculated insertion path while compensating for the tracked movement of the live body part, and after insertion of the probe along the insertion path, followed by withdrawal of the probe from the live body-part, sending a plurality of control commands to a robotic arm, which is attached to the probe and configured to manipulate the probe, to reinsert the probe in the live body part the calculated reinsertion path.

Still further in accordance with an embodiment of the present disclosure, the calculating of the reinsertion path is performed based on the calculated insertion path while compensating for the tracked movement of the live body-part during the insertion and the reinsertion of the probe in the live body part.

Additionally in accordance with an embodiment of the present disclosure, the method includes calculating a movement-compensated insertion path of the probe in the live body part based on the tracked movement of the probe during the insertion of the probe compensated by the tracked movement of the live body part during the insertion of the probe, and calculate the reinsertion path based on the movement-compensated insertion path further compensated by the tracked movement of the live body part during the reinsertion of the probe in the live body part.

Moreover, in accordance with an embodiment of the present disclosure, the probe includes an endoscope having a lens.

Further in accordance with an embodiment of the present disclosure, the method includes processing an image captured by the endoscope so as to detect a blur in the image that is indicative of a need to clean the lens.

Still further in accordance with an embodiment of the present disclosure, the method includes sending a command to the robotic arm to remove the endoscope from the live body part for cleaning in response to detecting the blur in the image captured by the endoscope.

Additionally, in accordance with an embodiment of the present disclosure, the method includes automatically cleaning the lens of the endoscope after the endoscope had been removed from the live body-part.

Moreover, in accordance with an embodiment of the present disclosure, sending the plurality of control commands to the robotic arm to reinsert the probe in the live body part the calculated reinsertion path is performed in response to the lens being automatically cleaned.

Further in accordance with an embodiment of the present disclosure, the method includes outputting a notification that the lens of the endoscope needs cleaning.

There is also provided in accordance with still another embodiment of the present disclosure, a software product, including a non-transient computer-readable medium in which program instructions are stored, which instructions, when read by a central processing unit (CPU), cause the CPU to calculate an insertion path of a probe in a live body part based on tracked movement of the probe during an insertion of the probe in the live body-part, calculate a reinsertion path of the probe based on the calculated insertion path while compensating for tracked movement of the live body part including movement of the live body-part during the insertion and the reinsertion of the probe in the live body part, and after insertion of the probe along the insertion path, followed by withdrawal of the probe from the live body-part, send a plurality of control commands to a robotic arm, which is attached to the probe and configured to manipulate the probe, to reinsert the probe in the live body part the calculated reinsertion path.

BRIEF DESCRIPTION OF THE DRAWINGS

The present invention will be understood from the following detailed description, taken in conjunction with the drawings in which.

DESCRIPTION OF EXAMPLE EMBODIMENTS

Overview

Figure 1:
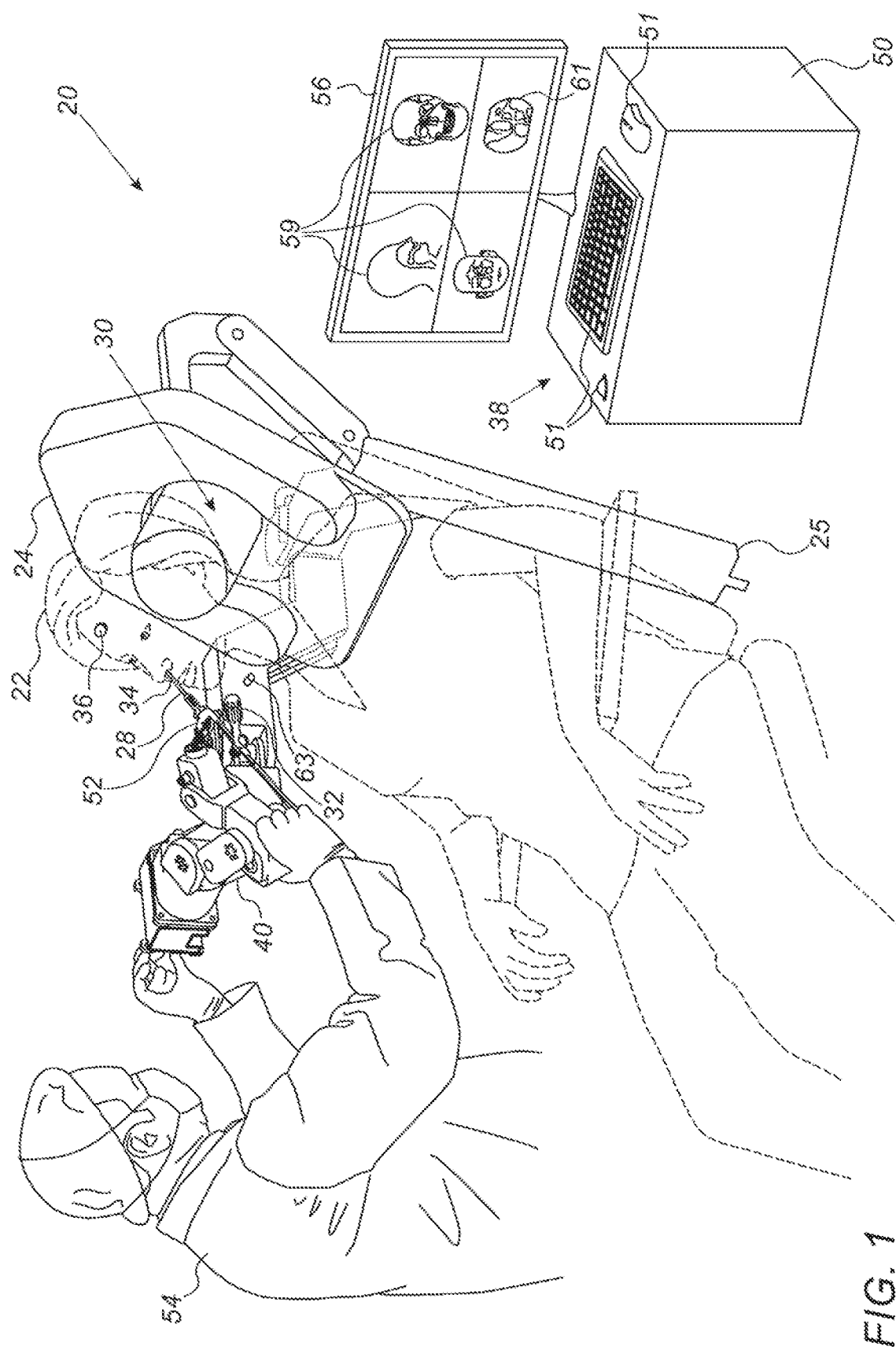
FIG. 1 is a schematic illustration of a surgery system, according to an embodiment of the present invention.

By way of introduction, an endoscope needs to be carefully maneuvered by a physician during a medical procedure. However, the physician generally needs both hands free for other surgical tasks. Therefore, the physician may ask his assistant to hold and guide the endoscope. The task of holding and guiding the endoscope may be challenging to perform accurately and quickly. Robots may ease this task by grasping the endoscope and hold the endoscope in place when required, thereby making handling somewhat easier. Nevertheless, the removal of an endoscope (e.g., for cleaning) and reinsertion (e.g., after cleaning) even with the help of a robot may not be simple since the path followed by the endoscope tip is often tortuous, and may be further complicated by movement of a patient's head or another body part.

Therefore, in accordance with embodiments of the present invention, a robot is used to manipulate the endoscope to provide automated removal of the endoscope, for example, to facilitate cleaning the endoscope lens, and automated reinsertion of the endoscope (after the lens has been cleaned) based on tracking the movement of the endoscope during insertion of the endoscope in a body part along with tracking movement of the body part, as will be explained in more detail below.

An insertion path of the endoscope in the live body-part is calculated based on the tracked movement of the endoscope during the insertion. During initial insertion of the endoscope, the robot can be set to provide little resistance so that the endoscope may be inserted manually, e.g., by the physician, and once the endoscope is correctly positioned in the body part the arms of the robot are held rigid to hold tool in place. Automated methods of inserting the endoscope may be employed in some embodiments.

When the endoscope lens needs cleaning, the endoscope may be removed by the robot based on the tracked insertion path while compensating for the tracked movement of the body part. After the lens has been cleaned, the endoscope may be reinserted by the robot along a reinsertion path based on the calculated insertion path while compensating for the tracked movement of the live body part. The paths followed by the robot are based on the tracked movement of the endoscope and the tracked movement of the body part so that even if the body part moves during insertion, removal and/or reinsertion of the endoscope, and/or any time between insertion, removal and/or reinsertion of the endoscope, the movement of the body part is compensated for when calculating the removal and reinsertion paths. Alternatively, automated removal and reinsertion of the endoscope using the apparatus and methods described herein may be performed for other purposes, not necessarily associated with cleaning the endoscope lens.

Blurring of the lens due to steam, blood or other substances, may be detected automatically by a controller or by the physician observing that the image captured by the endoscope is blurred. Removal of the endoscope is typically performed automatically as a response to detecting that the lens is blurred or based on a manual selection made by the physician. In some embodiments, the endoscope may be manually removed by the physician. The lens may be cleaned automatically by the robot using a water jet and/or other cleaning tool. Alternatively, the lens may be manually cleaned by the physician, for example, by wiping the lens with gauze.

The above embodiments have been described with respect to an endoscope, but the embodiments of the present invention may also be implemented to provide automatic removal and/or reinsertion of any suitable probe in a body part.

System Description

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

Figure 2:
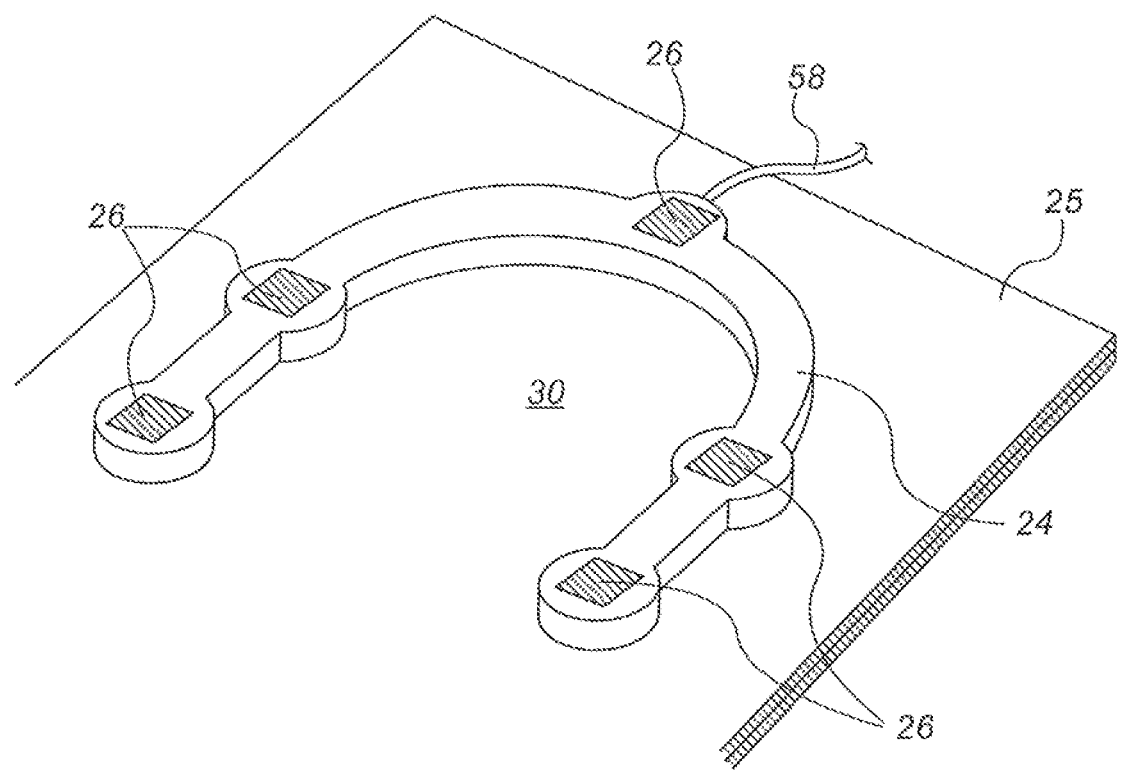
FIG. 2 is a schematic illustration of a magnetic field radiation assembly used in the surgery system, according to an embodiment of the present invention.

Turning now to the drawings, reference is now made to FIG. 1, which is a schematic illustration of a surgery system 20, and to FIG. 2, which is a schematic illustration of a magnetic field radiation assembly 24 used in the system 20, according to an embodiment of the present invention. The surgery system 20 is typically used during an invasive and/or investigative procedure on a nasal sinus or another body part (such as the brain) of a patient 22.

For the procedure, the magnetic field radiation assembly 24 may be positioned behind and/or around the head of the patient 22, for example by fixing the assembly 24 to a chair 25 (or bed) upon which the patient is sitting (or lying). The magnetic field radiation assembly 24 in the pictured example comprises five magnetic field radiators 26, which are fixed in a horseshoe shaped frame, the frame being positioned beneath or around the patient 22 so that the magnetic field radiators 26 surround the head of the patient 22. Alternatively, smaller or larger numbers of radiators 26 may be used, in various different configurations. The magnetic field radiators 26 are configured to radiate alternating magnetic fields at respective frequencies into a region 30, in proximity to the magnetic field radiation assembly 24 and which includes the head of patient 22. The alternating magnetic fields induce signals in a sensor 32 and a sensor 36. The sensor 32 is shown disposed on a probe 28 in order to track movement of the probe 28. The probe 28 is attached to and held by a robotic arm 40, which is configured to manipulate the probe 28. The sensor 36 is shown disposed on the forehead of the patient 22 in order to track movement of the head of the patient 22.

Each sensor 32, 36 typically includes a set of three orthogonal coils, and the signals may be analyzed by a controller 38 to derive the location and orientation of the sensors 32, 36 with respect to the magnetic field radiation assembly 24. It will be understood that the location and orientation of sensors 32, 36 may be determined for substantially any positioning of the sensor within region 30.

As is described in more detail below, sensor 32 is affixed to the probe 28, and determination of the location and orientation of the sensor 32 enables the location and orientation of a distal end 34 of the probe 28, that may be reversibly inserted into a live body-part of the patient 22, to be tracked. The sensor 32 is configured to track movement of the probe 28 during insertion and a reinsertion (e.g., after cleaning the probe 28) of the probe 28 in the live body-part. When the probe 28 is a rigid probe, the sensor 32 may generally be disposed on any suitable part of the probe 28 (e.g., the distal end 34 or on a proximal end 52 of the probe 28) and/or on the robotic arm 40 which is holding the probe 28. If the distal end 34 of the probe 28 is flexible, the sensor 32 is generally disposed on the distal end 34 of the probe 28 in order to accurately track the movement of the distal end 34 of the probe 28. By way of example only, the probe 28 may include an endoscope having a lens.

Similarly, determination of the location and orientation of the sensor 36 enables the location and orientation of the live body-part (e.g., head) of the patient 22 to be tracked. Therefore, the sensor 36 is configured to track movement of the live body-part, including movement of the live body-part during the insertion and the reinsertion of the probe 28 in the live body-part. The sensor 36 is shown in FIG. 1 as being disposed on the forehead of the patient 22. The sensor 36 may be disposed on any other suitable body part of the patient 22 in order to track movement of the patient 22.

A system using magnetic field radiators, such as the magnetic field radiators 26, for tracking an entity inserted into a patient is described in US Patent Publication 2016/0007842, issued as U.S. Pat. No. 10,772,489 on Sep. 15, 2020, of Govari et al., which is incorporated herein by reference. In addition, the Carto® system produced by Biosense Webster of 33 Technology Drive, Irvine, Calif. 92618 USA, uses a tracking system similar to that described herein for finding the location and orientation of a coil in a region irradiated by magnetic fields.

The robotic arm 40 generally has its own robotic coordinate system. The robotic coordinate system is registered with a magnetic coordinate system of the magnetic field radiators 26 and/or vice-versa. Registration of the robotic coordinate system with the magnetic coordinate system may be performed, for example, by moving the robotic arm 40, or the probe 28 attached to the robotic arm 40, to one or more locations known to the magnetic field radiators 26, for example, to a location on the magnetic field radiation assembly 24 or to the sensor 36 or to one or more other known locations on the patient 22. Once registration of the robotic coordinate system with the magnetic coordinate system has been performed, locations in the magnetic coordinate system can be translated to the robotic coordinate system in order to manipulate the robotic arm 40 correctly.

Elements of system 20, including radiators 26, may be controlled by the controller 38, which comprises a processing unit communicating with one or more memories. Typically, the elements may be connected by cables to the controller 38, for example, radiators 26 may be connected by a cable 58 to the controller 38. Alternatively, or additionally, the elements may be coupled wirelessly to the controller 38. The controller 38 may be mounted in a console 50, which comprises operating controls 51 that typically include a keypad and/or a pointing device such as a mouse or trackball. The console 50 also connects to other elements of the surgery system 20, such as the proximal end 52 of the probe 28. A physician 54 uses the operating controls 51 to interact with the controller 38 while performing the procedure, and the controller 38 may present results produced by system 20 on a display screen 56. In FIG. 1 the display screen 56 is displaying various views 59 of a previous CT scan (or other suitable scan) which may be used as an aid for the physician 54 to guide the probe 28 in the body-part. The display screen 56 also shows an image 61 captured by the probe 28.

In practice, some or all of these functions of the controller 38 may be combined in a single physical component or, alternatively, implemented using multiple physical components. These physical components may comprise hard-wired or programmable devices, or a combination of the two. In some embodiments, at least some of the functions of the processing circuitry may be carried out by a programmable processor under the control of suitable software. This software may be downloaded to a device in electronic form, over a network, for example. Alternatively, or additionally, the software may be stored in tangible, non-transitory computer-readable storage media, such as optical, magnetic, or electronic memory.

The surgery system 20 may also include a lens cleaning device 63 configured to automatically clean the lens of the endoscope when an endoscope is included in the probe 28. The lens cleaning device 63 may comprise a water jet sprayer for spraying water on the lens or a wiper to wipe the lens with a suitable material, for example, but not limited to, a piece of gauze. The lens cleaning device 63 may be disposed on the robotic arm 40. Alternatively, or additionally, the lens cleaning device 63 may be implemented as part of the probe 28, for example, with a jet spray, which may be activated when the probe 28 is removed from the live body-part.

FIGS. 3A-C, 4, 5 describe the probe 28 as a rigid probe and the sensor 32 as a movable sensor which may be fixed to any suitable part of the probe 28 and therefore the location of the sensor 32 does not initially indicate the distal end 34 of the probe 28 until suitable calibration is performed. In some embodiments, the surgery system 20 may be implemented when the sensor 32 is integrated with the probe 28 and/or the position of the sensor 32 with respect to the distal end 34 of the probe 28 is already known. In other embodiments, the sensor 32 may be disposed on the robotic arm 40 and in such a case the location of the sensor 32 does not initially indicate the distal end 34 of the probe 28 until suitable calibration is performed.

Figures 3A, 3B, 3C:
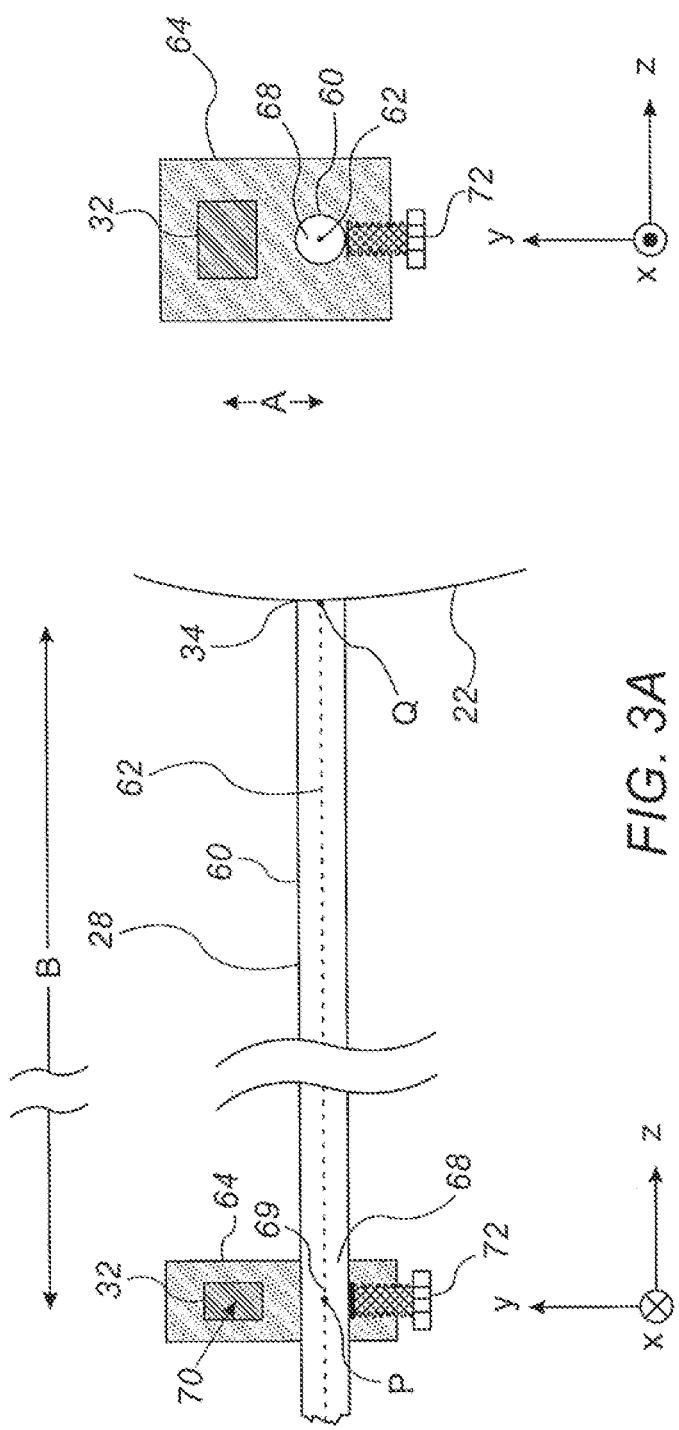
FIG. 3A is a schematic cross-sectional side view of an exemplary probe.
FIG. 3B is a schematic cross-sectional front view of the probe of FIG. 3B.
FIG. 3C is a schematic diagram illustrating vectors related to the probe of FIGS. 3A and 3B, according to an embodiment of the present invention.

FIG. 3A is a schematic cross-sectional side view of the probe 28, FIG. 3B is a schematic cross-sectional front view of the probe 28, and FIG. 3C is a schematic diagram illustrating vectors related to the probe 28, according to an embodiment of the present invention. In the following description of the probe 28, the probe 28 is assumed to comprise a rigid cylinder 60, having a longitudinal symmetry axis 62. In FIGS. 3A and 3B the probe 28 has been drawn on a set of xyz orthogonal axes, with the longitudinal symmetry axis 62 defining the z-axis. For clarity, in FIGS. 3A and 3B the xyz axes of the probe 28 are drawn displaced from the cylinder 60.

The sensor 32 is fixed to the cylinder 60 by a sensor holder 64, which is typically formed from plastic so as to completely encapsulate the sensor 32. As explained herein, signals from the sensor 32, generated in response to the magnetic fields interacting with the sensor 32, are used to determine a location and an orientation of the sensor 32. Conducting wires that convey the signals from the sensor 32 may be connected to the proximal end 52 of the probe 28, and from there to the console 50. The conducting wires are not shown in FIGS. 3A and 3B.

The sensor 32 is assumed to have a sensor direction 70, typically, but not necessarily, the direction of an internal axis of symmetry of the sensor 32, and the orientation referred to herein measures the orientation of the sensor direction with respect to a frame of reference defined by the magnetic field radiators 26 (FIG. 2). The sensor direction 70 of the sensor 32 is shown schematically in FIGS. 3A and 3C as an arrow.

The sensor holder 64 is produced to have a hole 68, which is formed to have a diameter substantially the same as that of cylinder 60, but sufficiently different so that there is a sliding fit between the holder 64 and the cylinder 60. When the holder 64 is produced, a center of the hole 68 is made to be a known distance A from the sensor 32. A typical value of A is 0.5 cm, but A may be smaller or larger than this value. A series of sensor holders may be constructed, having holes that are dimensioned to tools having different diameters. In addition, by virtue of being comprised in the holder 64, the center of the hole 68 has a known orientation θ with respect to the sensor direction 70. There is thus a known displacement vector (A, θ), herein also termed vector V, from the sensor 32 to the center of the hole 68, as shown in FIG. 3C.

The hole 68 has an axis of symmetry 69 that is typically orthogonal to the vector V, and which by virtue of being formed when the holder 64 is produced, has a known direction φ with respect to the vector V (FIG. 3C).

As is also described below, in operating the system 20, the hole 68 of the sensor holder 64 is slid onto cylinder 60, and the holder 64 is fixed to the cylinder 60 when the holder 64 is close to the proximal end 52. It will be understood that in sliding the cylinder 60 within the hole 68, the axes 69 and 62 are coincident, and also coincide with direction ϕ. The holder 64 comprises a setscrew 72, having a head, which may be grasped by the physician 54 (FIG. 1). Using the head, the physician 54 is able to hand-tighten the setscrew to fix the holder 64 at a desired position along the cylinder 60. The distance from the center of the sensor 32 to the distal end 34 is assumed to be a distance B. Unlike distance A, distance B is not known when sensor holder 64 is fixed to cylinder 60, but as is described below in operation of system 20, the controller 38 is able to calculate distance B.

Figure 4:
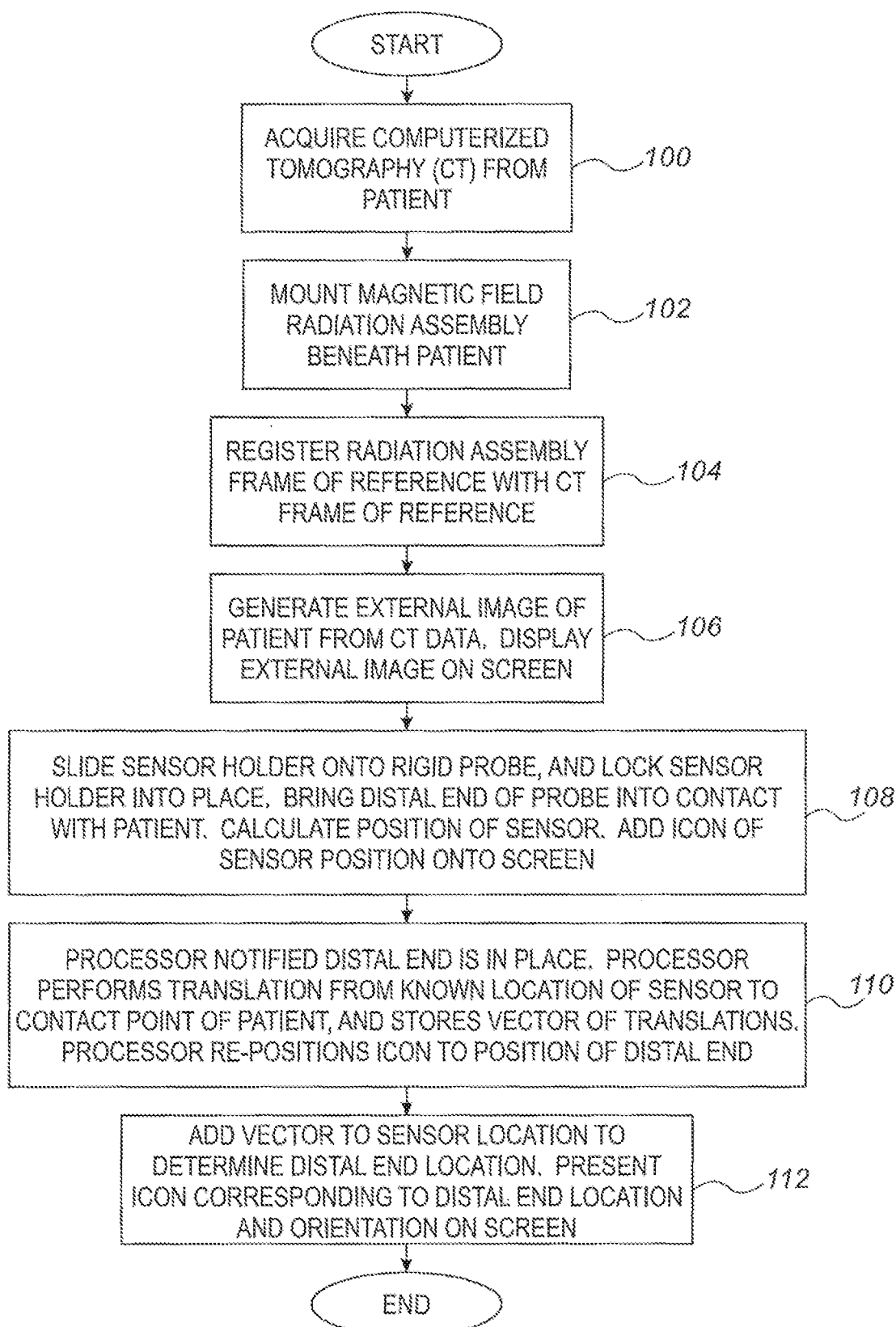
FIG. 4 is a flowchart including exemplary steps that are implemented in the operation of the surgery system of FIG. 1, according to an embodiment of the present invention.
Figure 5:
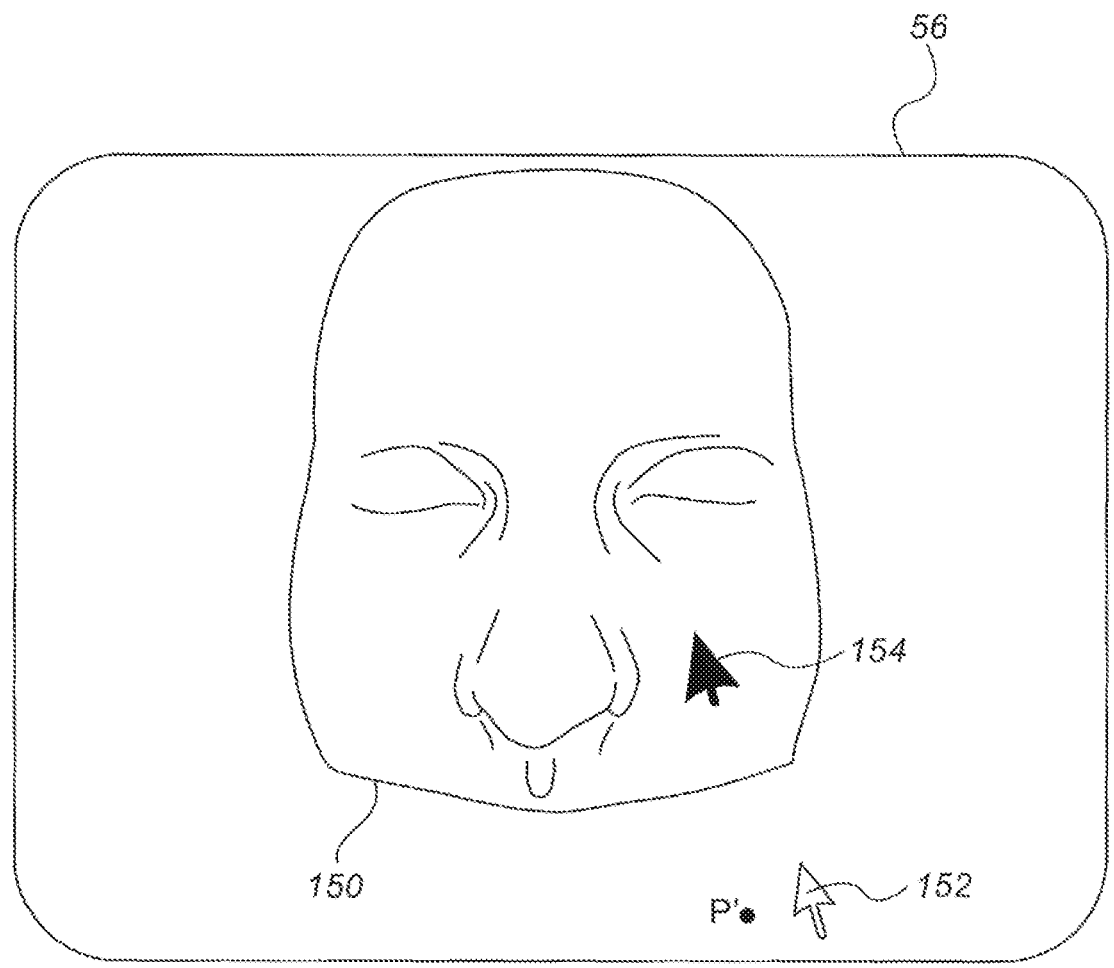
FIG. 5 is a schematic illustration of a screen used during implementation of the flowchart, according to an embodiment of the present invention.

FIG. 4 is a flowchart including exemplary steps that are implemented in the operation of the surgery system 20, and FIG. 5 is a schematic illustration of the display screen 56 during implementation of the flowchart, according to an embodiment of the present invention. The steps of the flowchart are also illustrated by FIGS. 1, 2, 3A, 3B, and 3C.

In an initial step 100, the head of patient 22 is scanned by computerized tomography (CT), herein by way of example assumed to be fluoroscopic CT, and the CT data from the scan is acquired by controller 38. The CT scan of patient 22 may be performed independently of the implementation of the remaining steps of the flowchart, which correspond to the surgical procedure. Typically, step 100 may be performed a number of days before the following surgical steps of the surgical procedure.

In a first procedure step 102, the radiation assembly 24 is mounted beneath or behind the head of the patient 22. Radiators 26 are then operated, and in a registration step 104, a frame of reference of the radiators 26 is registered with the frame of reference of the subject's head. The registration is typically performed by any means known in the art, e.g., by placing a magnetic field sensor coil such as the sensor 36, or a grouping of such coils, in one or more known locations and orientations with respect to the external features of the patient 22 as well as with the magnetic field radiation assembly 24 holding the radiators 26.

In an initial display step 106, controller 38 generates a representation 150, also referred to herein as image 150, of external features of the patient 22, using the CT data received in step 100. The CT data is in the form of voxels with Hounsfield units (HU), and the image 150 of the external features of patient 22 is generated from voxel values and their HU values. The controller 38 displays image 150 on the display screen 56, and FIG. 5 schematically illustrates the image 150 as displayed on the display screen 56.

In an operation step 108, the physician slides hole 68 of the sensor holder 64 onto the rigid cylinder 60 of the probe 28, and the physician 54 then uses setscrew 72 to lock the sensor holder in place, near proximal end 52 of the probe 28. Once the holder 64 is locked in place, the robotic arm 40 is set in a mode that allows manual movement of the robotic arm 40 by the physician 54. The physician 54 brings the distal end 34 of the probe 28 into contact with a selected region of the external features of the patient 22, for example a region at the side of the patient's nose.

The positioning of the distal end 34 brings the sensor holder 64 and its encapsulated sensor 32 into the region 30, so that the controller 38 is able to calculate the location and orientation of the sensor 32. Once the controller 38 has performed this calculation, it typically introduces an icon 152, representative of sensor direction 70, onto the display screen 56, in proximity to image 150. The icon 152 is located and orientated on the display screen 56 in accordance with the location and orientation of the sensor 32, determined from the sensor signals, within the common frame of reference of the image 150 and the magnetic field radiators 26.

By virtue of the fact that the physician 54 is manipulating the probe 28, the physician 54 is aware of the actual location and orientation of the sensor 32. Comparison of the location and orientation of icon 152 with the actual location and orientation of sensor 32 provides confirmation to the physician 54 of the correct operation of the surgery system 20.

In a calibration step 110, the physician 54 notifies the controller 38 that the distal end 34 of the probe 28 is in contact with an external feature of the patient 22, typically by using controls 51. On receipt of the notification, the controller 38 performs two translations on the known location of the sensor 32. A first translation corresponds to vector V (A, θ), (FIG. 3C) so that the controller 38 translates the location of the sensor 32 by a value A along a direction defined by θ to a point P on axis 62 (FIG. 3A). A point P', corresponding to point P, is drawn in FIG. 5, to illustrate the termination of the first translation. Typically, point P' is not drawn on screen 56.

From point P, the controller 38 performs a second translation, in a direction corresponding to direction ϕ. Since the axes 69 and 62 are coincident, the second translation is in a direction corresponding to translating along the axis 62. The controller 38 uses the data for the image 150 to determine the actual length of the second translation, by determining from the image data where point P, moving in direction ϕ along axis 69, meets an external surface of patient 22. The meeting with the external surface occurs when there is at least a predetermined change in radiodensity as measured in the image, e.g., a change in the value of the Hounsfield units of the image data. Suitable values for the change are 200-500 Hounsfield units. The meeting is assumed to be at a point Q on axis 62. Point Q is at a distance B, now known, from point P, and the second translation thus corresponds to a vector (B, ϕ), herein also termed vector W, and illustrated in FIG. 3C.

It will be understood that even though the calculation of the position of point Q uses CT image data, since the image 150 is registered with the actual external features of patient 22, point Q corresponds with an actual external point of the patient 22.

At the conclusion of the calibration step, the controller 38 deletes icon 152 from screen 56, and positions an icon 154 at a position on the image 150 corresponding to point Q. Comparison of the location and orientation of the icon 154 with the actual location and orientation of the distal end 34 provides confirmation to the physician 54 of the correct completion of the calibration step.

The sum of the two translations, V+W, of the calibration step is a vector that is stored by the controller 38.

In a continuing tracking step 112, the controller 38 adds the vector stored in step 110 to the location of the sensor 32 in order to determine the location of distal end 34. The orientation of the distal end 34 corresponds to direction ϕ, which is also determined by the controller 38 in tracking the sensor 32. Thus, the controller 38 is able to calculate the location and orientation of the distal end 34 by determining the location and orientation of the sensor 32. The controller 38 may position an icon corresponding to the location and orientation of the distal end 34 on the display screen 56. In some embodiments, if the distal end 34 is within patient 22, the external features of image 150 that may obscure the icon are rendered at least partially transparent. The position of the distal end 34 with respect to anatomic features of the patient 22 may be derived based on the calculated position of the distal end 34 with respect to coordinates on the registered image. In the above manner the distal end 34 of the probe 28 may be guided into the body-part of the patient 22 to a desired location by observation the movement of the icon in the captured CT or other images.

In some embodiments, the distal end 34 of the probe 28 may be guided into the body-part automatically by the robotic arm 40 based on a suitable path-finding algorithm. An example algorithm is described with reference to US Published Patent Application No. 2017/0056112A1, issued as U.S. Pat. No. 10,188,465 on Jan. 29, 2019, of Gliner, et al. which is herein incorporated by reference.

Figure 6:
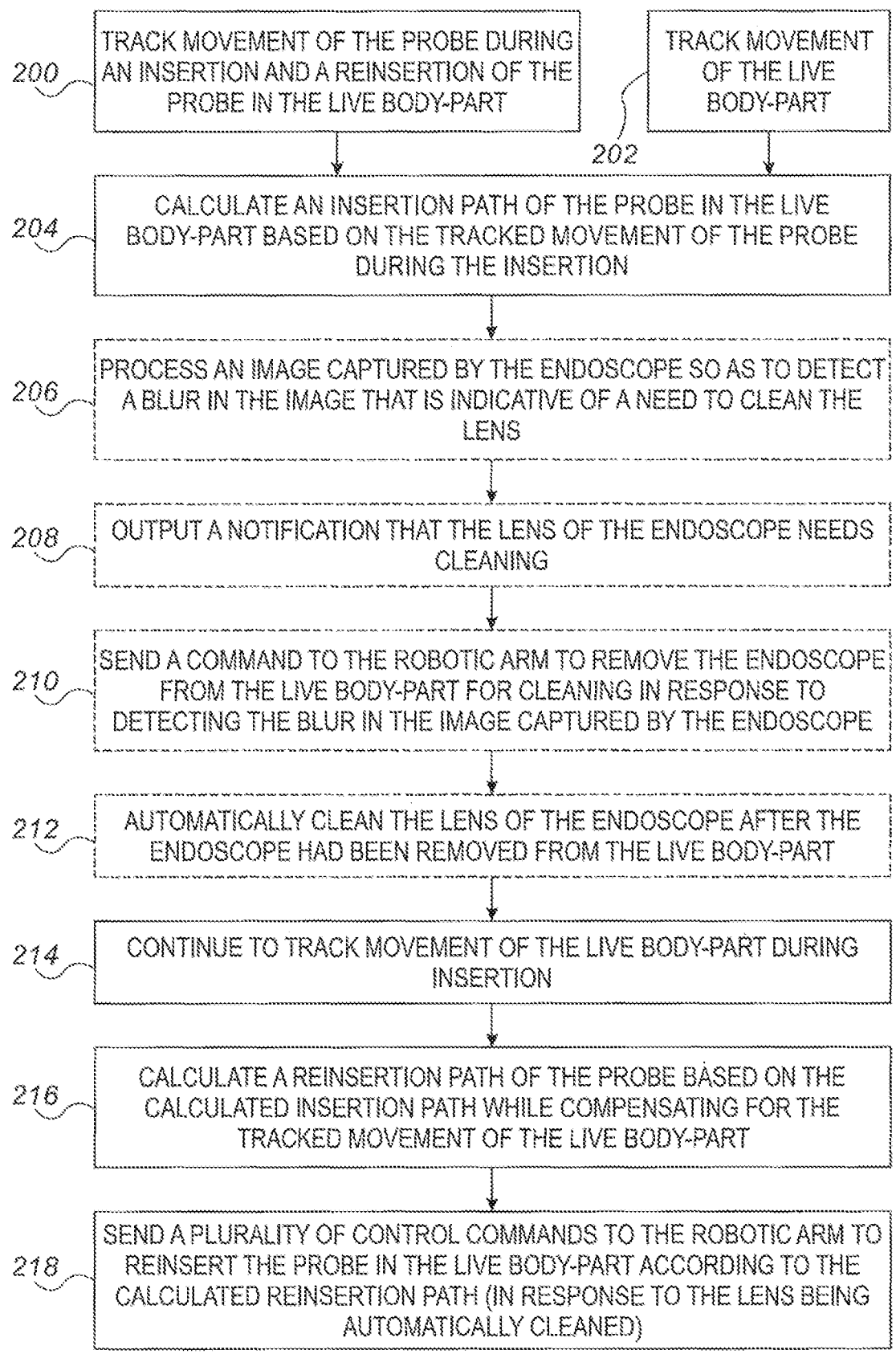
FIG. 6 is a flowchart including exemplary steps in a method for use in the surgery system of FIG. 1.

Reference is now made to FIG. 6, which is a flowchart including exemplary steps in a method for use in the surgery system 10 of FIG. 1. Reference is also made to FIG. 1. The sensor 32 is configured to track movement (block 200) of the probe 28 during an insertion and a reinsertion of the probe 28 in the live body-part. The sensor 36, disposed on the live body-part, is configured to track movement (block 202) of the live body-part including movement of the live body-part during the insertion and the reinsertion of the probe 28 in the live body-part.

The controller 38 is configured to calculate (block 204) the insertion path of the probe 28 in the live body-part based on the tracked movement of the probe 28 during the insertion. In some embodiments, the controller 38 is configured to calculate a movement-compensated insertion path of the probe 28 in the live body-part based on the tracked movement of the probe 28 during the insertion of the probe 28 compensated by the tracked movement of the live body-part during the insertion of the probe 28.

In accordance with some embodiments, the controller 38 is configured to process (block 206) images captured by the endoscope, included in the probe 28, so as to detect a blur in one or more of the images that is indicative of a need to clean the lens of the endoscope. Detecting blur may be performed using a Fast Fourier Transform of the image(s) and examining the distribution of low and high frequencies where a low amount of high frequencies may indicate that the image(s) is blurred. The controller 38 may be configured to output (block 208) a notification that the lens of the endoscope needs cleaning to the display screen 56.

In accordance with other embodiments, the physician 54 may detect that the lens is dirty based on observing blurring of the image 61 displayed on the display screen 56.

In accordance with some embodiments, the controller 38 is configured to send (block 210) a command to the robotic arm 40 to remove the probe 28 (including the endoscope) from the live body-part for cleaning in response to detecting the blur in the image captured by the endoscope or in response to a selection performed by the physician 54 via the operating controls 51. The robotic arm 40 is configured to remove the probe 28 according to the calculated insertion path as adjusted for by tracked movement of the live body-part from when each section of the insertion path was originally recorded until now. In accordance with some embodiments, the probe 28 may be removed manually by the physician 54.

After the endoscope had been removed from the live body-part, the lens cleaning device 63 is configured to automatically clean (block 212) the lens of the endoscope after the endoscope had been removed from the live body-part. In accordance with some embodiments, the physician 54 manually cleans the endoscope lens with a piece of gauze and/or with a water jet, by way of example only.

The sensor 32 and sensor 36 are configured to continue (block 214) to track the movement of the probe 28 and the live body-part during reinsertion of the probe 28 in the live body-part so as to continually adjust for new movement of the live body-part during the reinsertion of the probe 28.

The controller 38 is configured to calculate (block 216) a reinsertion path of the probe 28 based on the calculated insertion path while compensating for the tracked movement of the live body-part. In accordance with some embodiments, the controller 38 is configured to calculate the reinsertion path of the probe 28 based on the calculated insertion path while compensating for the tracked movement of the live body-part during the insertion and the current reinsertion of the probe 28 in the live body-part. In accordance with other embodiments, the controller 38 is configured to calculate the reinsertion path based on the movement-compensated insertion path further compensated by the tracked movement of the live body-part during the current reinsertion of the probe 28 in the live body-part.

After insertion of the probe 28 along the insertion path, followed by withdrawal of the probe 28 from the live body-part, the controller 38 is configured to send (block 218) control commands to the robotic arm 40 to reinsert the probe 28 in the live body-part according to the calculated reinsertion path. The step of block 218 may be performed in response to the lens being automatically cleaned by the lens cleaning device 63 or in response to receiving a manual selection from the physician 54 via the operating controls 51.

The steps of blocks 214, 216 and 218 are typically performed simultaneously. For example, as the probe 28 is being reinserted into the live body-part by the robotic arm 40, the movement of the live body-part is continually being tracked and the reinsertion path is continually being amended to compensate for the tracked movement of the live body-part. Similarly, the controller 38 is continually sending control commands to the robotic arm 40 to reinsert the probe 28 according to the most recent calculations of the reinsertion path.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and subcombinations of the various features described hereinabove, as well as variations and modifications thereof which would occur to persons skilled in the art upon reading the foregoing description and which are not disclosed in the prior art.

What is claimed is:

1. An automated system comprising:
   (a) an endoscope comprising a lens configured to be inserted into a live body-part and capture at least one image;
   (b) a lens cleaning device configured to automatically clean the lens of the endoscope;
   (c) a robotic arm attached to the endoscope and configured to manipulate the endoscope;
   (d) a first sensor configured to track movement of the endoscope during an insertion and a reinsertion of the endoscope in the live body-part;
   (e) a second sensor configured to track movement of the live body-part; and (f) a controller configured to:
responsive to identifying a blur in the at least one image, send one or more control commands to the robotic arm to remove the endoscope from the live body-part,
(ii) send one or more control commands to the lens cleaning device to clean the lens after the endoscope had been removed from the live body-part,
(iii) calculate an insertion path of the endoscope in the live body-part based on the tracked movement of the endoscope during the insertion;
(iv) calculate a reinsertion path of the endoscope based on the calculated insertion path while compensating for the tracked movement of the live body-part; and
(v) send one or more control commands to the robotic arm to reinsert the endoscope in the live body-part according to the calculated reinsertion path.

2. The system according to claim 1, wherein identifying a blur in the at least one image comprises the controller processing an image captured by the endoscope so as to detect the blur in the at least one image.

3. The system according to claim 1, wherein the controller is configured to output a notification that the lens of the endoscope needs cleaning.

4. The system according to claim 1, wherein the controller is configured to instruct the robotic arm to automatically remove the endoscope from the live body-part.

5. The system according to claim 1, wherein sending a plurality of control commands to the robotic arm to reinsert the endoscope in the live body-part according to the calculated reinsertion is responsive to the lens being automatically cleaned.

6. The system according to claim 1, wherein at least part of the endoscope is flexible, and wherein the first sensor is disposed on a distal end of the endoscope.

7. The system according to claim 1, wherein the controller is further configured to calculate a removal path of the endoscope based on the calculated insertion path while compensating for the tracked movement of the live body-part during the removal of the endoscope from the live body-part.

8. The system according to claim 1, wherein the first sensor is moveable along the endoscope.

9. The system according to claim 1, wherein the endoscope includes a rigid cylinder, wherein the first sensor is removably coupled with the rigid cylinder of the endoscope.

10. The system according to claim 1, further comprising a magnetic field radiation assembly configured to surround a head of a patient.

11. The system according to claim 10, wherein the magnetic field radiation assembly includes a plurality of magnetic field radiators configured to radiate alternating magnetic fields at respective frequencies into a region that includes the head of a patient, wherein the alternating magnetic fields are configured to induce signals in the first and second sensors.

12. The system according to claim 11, wherein the first and second sensors each comprise at least first and second coils disposed perpendicular to one another, wherein the controller is configured to derive a location and an orientation of the first and second sensors with respect to the magnetic field radiation assembly in response to the signals.

13. A method comprising:
responsive to identifying a blur in at least one image, sending a plurality of control commands, using a processor, to a robotic arm to remove an endoscope configured to capture at least one image from a live body-part;
responsive to the endoscope being removed from the live body-part, sending a plurality of control commands, using the processor, to a lens cleaning device to clean a lens of the endoscope after the endoscope has been removed from the live body-part;
calculating, using the processor, an insertion path of the endoscope during the insertion in the live body-part based on tracked movement data from a first sensor;
calculating, using the processor, a reinsertion path of the endoscope based on the insertion path and tracked movement data from a second sensor; and
sending a plurality of control commands to the robotic arm to reinsert the endoscope in the live body-part according to a calculated reinsertion path.

14. The method of claim 13, wherein identifying a blur in the at least one image comprises processing, using the processor, an image captured by the endoscope so as to detect the blur in the at least one image.

15. The method of claim 13, further comprising, outputting, using the processor, a notification that the endoscope needs cleaning.

16. An apparatus comprising:
(a) a processor, and
(b) a memory storing instructions that cause the processor to:
(i) responsive to identifying a blur in at least one image, send a plurality of control commands to a robotic arm to remove an endoscope from a live body-part,
(ii) send a plurality of control commands to a lens cleaning device to clean a lens of the endoscope after the endoscope has been removed from the live body-part,
(iii) calculate an insertion path of the endoscope during the insertion in the live body-part based on tracked movement data from a first sensor,
(iv) calculate a reinsertion path of the endoscope based on the insertion path and tracked movement data from a second sensor, and
(v) send a plurality of control commands to the robotic arm to reinsert the endoscope in the live body-part according to a calculated reinsertion path.

17. The method according to claim 13, further comprising calculating, using the processor, a removal path of the endoscope based on the calculated insertion path while compensating for the tracked movement of the live body-part during the removal of the endoscope from the live body-part.

18. The method according to claim 13, further comprising radiating, using a magnetic field radiation assembly, alternating magnetic fields at respective frequencies into a region that includes the head of a patient, wherein the alternating magnetic fields are configured to induce signals in the first and second sensors, wherein the first and second sensors each comprise at least first and second coils disposed perpendicular to one another, wherein the controller is configured to derive a location and an orientation of the first and second sensors with respect to the magnetic field radiation assembly in response to the signals.

19. The apparatus according to claim 16, wherein the instructions further cause the processor to calculate a removal path of the endoscope based on the calculated insertion path while compensating for the tracked movement of the live body-part during the removal of the endoscope from the live body-part.

20. The apparatus according to claim 16, further comprising a magnetic field radiation assembly configured to surround a head of a patient and include a plurality of magnetic field radiators configured to radiate alternating magnetic fields at respective frequencies into a region that includes the head of a patient, wherein the alternating magnetic fields are configured to induce signals in the first and second sensors, wherein the first and second sensors each comprise at least first and second coils disposed perpendicular to one another, wherein the controller is configured to derive a location and an orientation of the first and second sensors with respect to the magnetic field radiation assembly in response to the signals.

\* \* \* \* \*